United States Patent

Ruka

[11] 4,088,543
[45] May 9, 1978

[54] TECHNIQUE FOR PROTECTING SENSING ELECTRODES IN SULFIDING ENVIRONMENTS

[75] Inventor: Roswell J. Ruka, Churchill Boro, Pa.

[73] Assignee: Westinghouse Electric Corp., Pittsburgh, Pa.

[21] Appl. No.: 722,259

[22] Filed: Sep. 10, 1976

[51] Int. Cl.² ............................................. G01N 27/46
[52] U.S. Cl. .................................. 204/1 T; 204/195 S
[58] Field of Search ................... 204/1 S, 1 F, 195 S; 324/29

[56] References Cited

U.S. PATENT DOCUMENTS

| | | | |
|---|---|---|---|
| 3,514,377 | 5/1970 | Spacil et al. | 204/1 T |
| 3,654,112 | 4/1972 | Beekmans et al. | 204/195 S |
| 3,699,032 | 10/1972 | Rapp | 204/195 S |
| 3,819,499 | 6/1974 | Hoogeveen et al. | 204/195 S |
| 3,923,624 | 12/1975 | Beekmans et al. | 204/195 S |
| 3,960,500 | 6/1976 | Ross et al. | 204/1 T X |

Primary Examiner—G. L. Kaplan
Attorney, Agent, or Firm—M. P. Lynch

[57] ABSTRACT

The deteriorating influence of sulfide environments on the sensing electrode of a conventional oxygen ion conductive solid electrolyte electrochemical cell is minimized by controllably introducing oxygen to the sensing electrode when the oxygen content of the environment to which the sensing electrode is exposed diminishes to a predetermined level, thereby avoiding undesirable cycling of the environment between oxidizing and sulfiding conditions.

1 Claim, 5 Drawing Figures

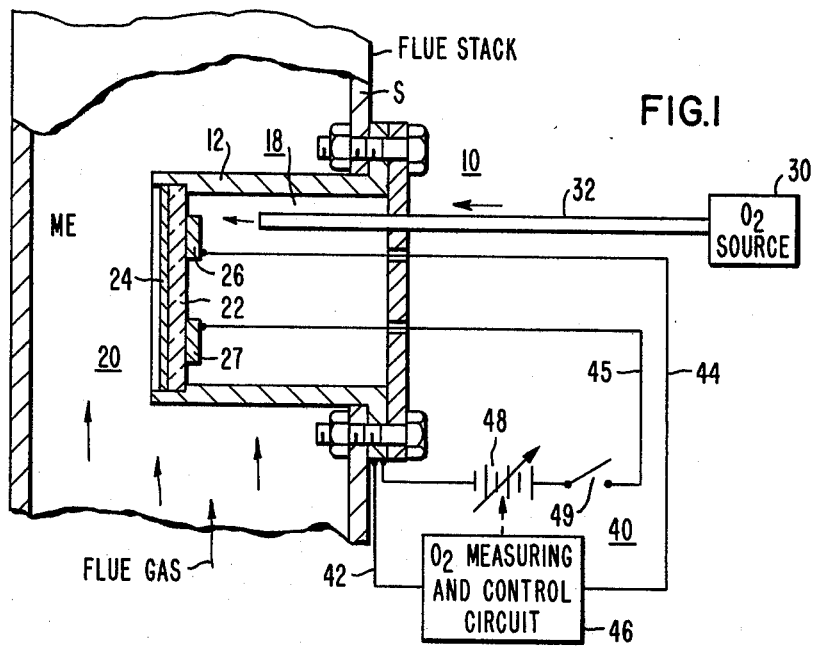

TECHNIQUE FOR PROTECTING SENSING ELECTRODES IN SULFIDING ENVIRONMENTS

BACKGROUND OF THE INVENTION

There is a practical need to extend the useful life of the electrodes associated with oxygen ion conductive solid electrolyte electrochemical cells used in flue gas streams of combustion systems. Power plant flue gases typically include sulfur-containing gases which, when insufficient oxygen is present, can produce adverse sulfiding of electrodes, which typically consist of platinum group metals, such as rhodium, palladium, iridium, platinum, etc., as well as silver. This sulfiding results in increased cell resistance and deteriorating cell operation.

Oxygen ion conductive solid electrolyte electrochemical cells constructed in accordance with the teachings of U.S. Pat. No. 3,400,054, issued Sept. 3, 1968, assigned to the assignee of the present invention, and incorporated herein by reference, typically operate over a temperature range of between approximately 600° C and 1100° to measure the oxygen content of a monitored environment. A platinum group electrode of a typical oxygen analyzer operating in this temperature range in a monitored environment containing an excess of oxygen and small quantities of sulfur compounds will evaporate slowly as an oxide, but the remaining electrode material remains largely that of the platinum group material and remains a useful electrode for an extended period of time.

However, if the flue gas environment contains a of fuel constituent, such as CO or $H_2$, in an amount in excess of that required for stoichiometric combustion, then sulfur compounds such as $H_2S$, COS, or S can form in the flue gas, react with the electrode material, and form sulfides which do not perform well as electrodes. If the monitored environment then returns to an oxidizing atmosphere, i.e., excess oxygen, pure platinum is reformed from the sulfide by reaction with oxygen. However, repeated excursions from oxidizing to sulfiding atmospheres eventually damage the performance of the electrode as manifested by an increase in the polarization resistance due to reduced contact of the electrode with the solid electrolyte material, spalling of the electrode, corrosion around the edge of the electrode, etc.

An oxidizing atmosphere is defined as an atmosphere in which sulfur-containing gases will not react with the sensing electrode material, i.e., platinum or silver, or metal connectors to form a sulfide.

SUMMARY OF THE INVENTION

There is disclosed herein with reference to the accompanying drawings several techniques avoiding the deteriorating influence of sulfiding atmospheres on electrodes of oxygen ion conductive solid electrolyte electrochemical cells.

In a preferred embodiment, an oxygen ion conductive solid electrolyte electrochemical cell includes a sensing electrode exposed to a flue gas environment capable of producing a sulfiding atmosphere, and an oxygen reference electrode and an oxygen transfer electrode isolated from the flue gas environment and exposed to a source of oxygen. An electrical circuit associated with the oxygen ion conductive solid electrolyte electrochemical cell includes a voltage measuring circuit for monitoring the EMF produced by the cell as an indication of the oxygen content of the flue gas environment and a cell voltage limiting circuit which operates only when the oxygen content level in the flue gas environment falls to a level at which the atmosphere can sulfide the sensing electrode. In a voltage limiting mode of operation the circuit converts the electrochemical cell to an oxygen "pump" whereby oxygen is transferred from the oxygen reference source through the electrolyte to the sensing electrode to maintain a predetermined protective oxygen, or oxidizing atmosphere, at the sensing electrode.

Alternatively oxygen may be supplied from an oxygen source directly to the sensing electrode via a conduit without employing the pumping operation of the electrochemical cell.

Yet another technique for protecting the sensing electrode from the adverse effects of a sulfiding atmosphere, consists of coating the sensing electrode with an intimate contacting layer of non-porous ceramic oxide which exhibits both ionic and electronic conductivity. A suitable ceramic oxide is cerium oxide, particularly as doped with rare earth oxides.

DESCRIPTION OF THE DRAWINGS

The invention will become more readily apparent from the following exemplary description in connection with the accompanying drawings:

FIG. 1 is a sectioned schematic illustration of an embodiment of the invention;

FIg. 2 is a modification to the embodiment of FIG. 1;

FIG. 3 is an alternate electrical circuit for use with the embodiment of FIG. 1 to achieve the desired oxygen pumping mode of operation;

FIG. 4 is an alternate embodiment of the invention; and

DESCRIPTION OF THE PREFERRED EMBODIMENT

Figure 5:
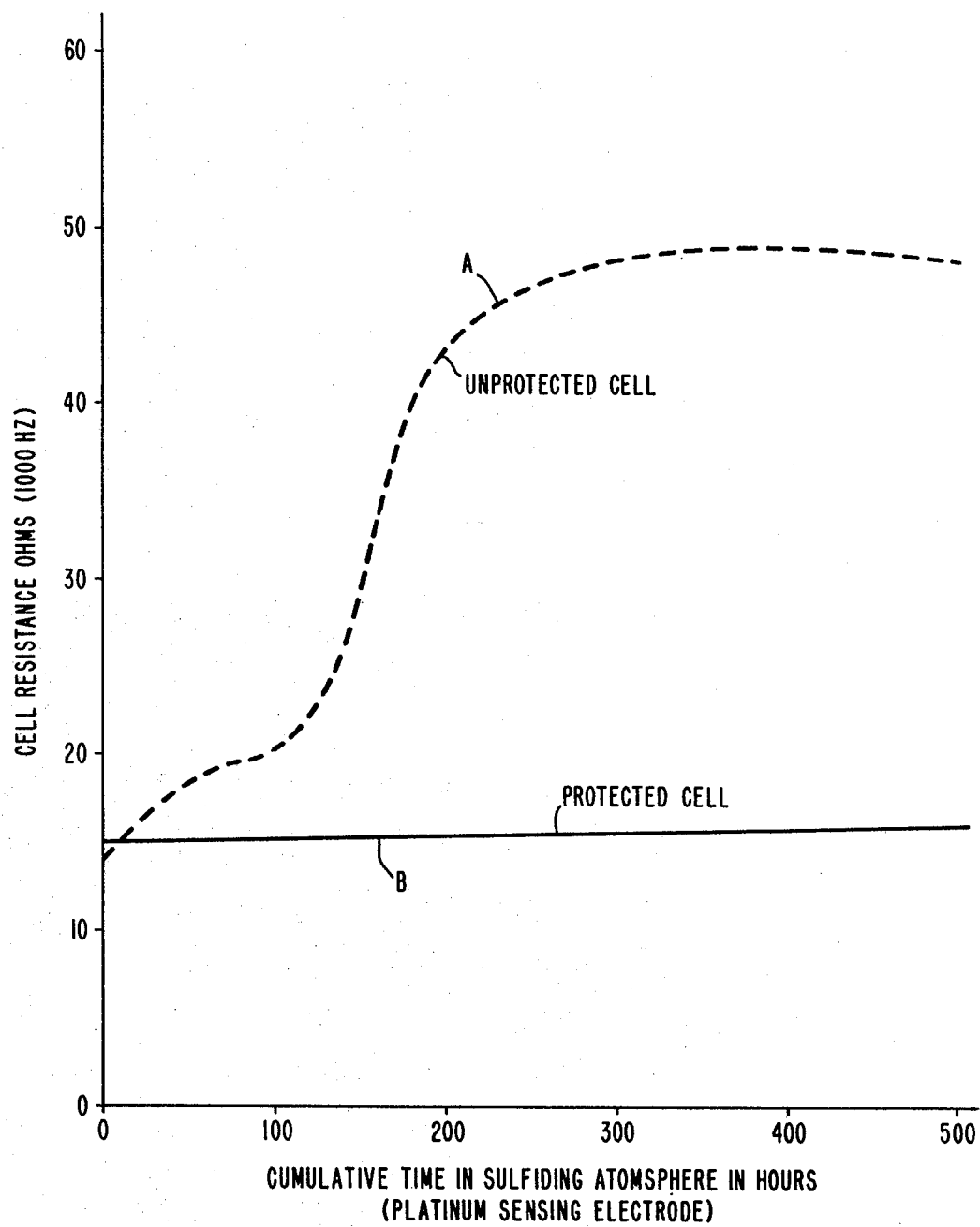
FIG. 5 is a graphical illustration of the improved operation of an oxygen ion conductive solid electrolyte electrochemical cell employing the inventive techniques.

Referring to FIG. 1, there is schematically illustrated an embodiment of the invention consisting of an oxygen probe assembly 10 inserted through the wall of a flue stack S to monitor the oxygen content of the flue gas present within the stack, herein identified as the monitored environment ME. The probe assembly 10 consists of an electrically conductive tubular housing 12 having a solid electrolyte electrochemical cell 20 forming the closed end of the tubular housing 12. Electrochemical cell 20, which corresponds to a conventional solid electrolyte electrochemical cell such as that identified in the above-referenced U.S. patent, consists of an oxygen ion conductive solid electrolyte 22, a sensing electrode 24 exposed to the monitored environment ME and an oxygen reference electrode 26 an an oxygen transfer electrode 27 exposed to the reference oxygen environment established in the reference chamber 18 of the tubular housing 12 by the flow of oxygen or an oxygen containing gas, such as air, from the oxygen source 30 through the supply tube 32. The electrodes 24, 26 and 27 are electrically connected to a voltage measuring and control circuit 40 via electrical conductors 42, 44 and 45, respectively. The probe assembly 10 measures the oxygen content of the monitored environment ME and develops an electrical signal indicative of the oxygen content for transmission to the voltage measuring and control circuit 40. This mode of operation is in accordance with solid electrolyte electrochemical cell oxygen analyzer techniques known in the art.

The modification to the conventional operation of the probe assembly 10 to satisfy the need to protect the sensing electrode 24 from deterioration due to a sulfiding atmosphere within the monitored environment ME is accomplished through the operation of the voltage measuring and control circuit 40. The circuit 40 consists of a voltage measuring circuit 46 and a controllable voltage source 48. In addition to manifesting the EMF developed by the electrochemical cell 20 to provide an indication of the oxygen content of the monitored environment ME, the voltage measuring circuit 46 includes a setpoint control such that an EMF signal indicative of a predetermined oxygen content level in the monitored environment will result in the closure of switch 49 and the activation of the variable voltage source 48. The predetermined oxygen content level may correspond to a level slightly above the level at which sulfiding of the sensing electrode 24 will occur. The application of a potential across the electrodes 24 and 27 by the variable voltage source 48 is of a polarity to cause the pumping or transfer of oxygen ions from the oxygen reference chamber 18 through the solid electrolyte 22 to the sensing electrode 24 to establish a minimum protective "oxygen cover" at the surface of the sensing electrode 24. This oxygen transfer ceases when the oxygen content of the monitored environment exceeds the preselected setpoint value. The pumped oxygen at the sensing electrode will dissipate within a few seconds after the pumping is terminated thus permitting a measurement of the oxygen content of the monitored environment ME.

Suitable implementation of the circuit 40 may be realized by the use of a commercially available meter relay for the voltage measuring circuit 46 wherein a variable setpoint on the meter relay can be used to actuate switch 49 and optionally to activate a motor for controlling the oxygen pumping operation by controlling the level of potential applied across the electrodes 24 and 27 by the variable voltage source 48. The opening of the switch 49 to discontinue the oxygen transfer to the sensing electrode 24 occurs when the "oxygen cover" satisfies the predetermined setpoint.

The voltage measuring circuit 46 then responds to the EMF developed across electrodes 24 and 26 by manifesting the oxygen content of the monitored environment ME.

While the function of circuit 40 has been implemented through the use of the most basic components for the purpose of clarity, it is obvious that the function of circuit 40 can be satisfied electronically.

Furthermore, while the oxygen reference electrode 26 and the oxygen transfer electrode 27 can be combined as a single electrode, the resistance and polarization losses likely to occur would be included in the cell voltage reading during the time periods when oxygen is being transferred to the sensing electrode 24, thus requiring compensation for these effects if accurately known oxygen protective atmospheres are to be achieved.

In applications of the embodiment of the invention disclosed in FIG. 1 wherein the volume of the monitored environment is substantial, thus requiring a significant oxygen pumping operation to establish the desired protective oxidizing atmosphere at the surface of the sensing electrode 24, it has proven useful to connect a volume adaptor 50 of the type illustrated in FIG. 2 to the end of the probe assembly 10 to define a secondary volume 52 adjacent to the sensing electrode 24. The adaptor 50 may be in the form of a porous membrane sufficient to permit passage of the flue gas from the monitored environment ME to the volume 52 or may be a metal or ceramic cap, as illustrated in FIG. 2, including apertures 54 which serve to transmit the flue gas from the monitored environment to the volume 52. The advantage of the volume adaptor 50 is that it limits the volume adjacent to the sensing electrodes 24 into which oxygen is pumped from the reference chamber 18. This reduces the level of voltage required from the variable voltage source 48 to achieve adequate oxygen pumping to establish the desired oxidizing atmosphere at the surface of the sensing electrode 24. An electrode separate from but adjacent to the sensing electrode 24 could be provided to cooperate with electrode 27 to pump oxygen. A structure similar to the volume adaptor 50 is illustrated in the gas measuring probe apparatus described in detail in U.S. Pat. 3,928,161, issued December 23, 1975, assigned to the assignee of the present invention, and included herein by reference.

A further departure from the embodiment of FIG. 1, as illustrated in FIG. 2, consists of an alternate technique for introducing the oxygen at the sensing electrode 24 to establish the desired protective "oxygen cover". This alternate technique bypasses the use of the solid electrolyte electrochemical cell 20 in a pumping mode and instead discloses the introduction of oxygen into the volume 52 from an oxygen source 55 via tubular member 56 extending through the wall of the volume adaptor 50. A flow control valve 57 responds to the setpoint condition developed by circuit 40 to establish the protective "oxygen cover" in accordance with the operation of circuit 40 described above.

The significant effect of the protective oxidizing atmosphere that is achieved in accordance with the embodiments of FIGS. 1 and 2 is graphically illustrated in FIG. 5. Curve A illustrates the significant change in AC resistance of an oxygen sensing cell having a platinum electrode exposed to alternating sulfiding and oxidizing atmospheres without the protective "oxygen cover". Curve B illustrates the AC resistance of a similar oxygen sensing cell having the benefit of a protective "oxygen cover" while operating in a monitored environment exhibiting a sulfiding atmosphere.

The appreciable AC resistance change of the unprotected cell is accompanied by spalling of the platinum electrode material after long periods of repeated excursions between oxidizing and sulfiding atmospheres.

FIG. 3 schematically illustrates an alternate implementation of the voltage measuring and control circuit 40 of FIG. 1. By maintaining the oxygen level in the oxygen reference chamber 18 at a level significantly greater than the anticipated oxygen content of the monitored environment ME, the resulting electrochemical cell EMF is of proper polarity and sufficient magnitude to sustain a useful level of oxygen transfer from the oxygen reference chamber 18 to the surface of the sensing electrode 24, when the cell 20 is shunted by a resistance, thereby achieving the desired protective oxidizing atmosphere. The pumping mode of operation is achieved via the shunting circuit 60 in response to a signal from the voltage measuring circuit 62 indicative of an oxygen level in the monitored environment ME corresponding to a near sulfiding atmosphere at the surface of the sensing electrode 24. The shunting circuit 60, which may be a manually or motor driven potentiometer, or a field effect transistor in an electronic circuit, responds to a signal from the voltage measuring circuit 62 by varying the resistance or conductance of the shunting circuit 60 to utilize the EMF generated by the cell 20 to pump oxygen from the oxygen reference chamber 18 to the surface of the sensing electrode 24. When the cell 20 is shunted by circuit 60, the molecular oxygen at the transfer electrode 27 is converted to oxygen ions which migrate through the electrolyte 22 and are released as molecular oxygen at the sensing electrode 24. Thus by controlling the current flow through the cell by circuit 60, the amount of oxygen transferred to the sensing electrode 24 is controlled.

Yet another approach to protecting the sensing electrode 24, which is indicated above as being a material from the platinum group including platinum, rhodium, palladium, iridium, etc. and also silver from the adverse effects of a sulfiding atmosphere, consists of the application of an intimate layer of a ceramic oxide 70 across the surface of the sensing electrode 24 as illustrated in FIG. 4. Studies have shown that the ceramic layer 70 may consist of a layer of mechanically non-porous ceramic such as cerium oxide, particularly if the non-porous ceramic is doped with small amounts of rare earths, such as praesodymium oxide or samarium oxide. The ceramic selected functions as an integral part of the electrode and must exhibit both ionic and electronic conductivity characteristics.

I claim:

1. A method of protecting the sensing electrode of an oxygen sensing solid electrolyte electrochemical cell from the deteriorating affects of a reducing atmosphere of a gas environment contacting said sensing electrode, said cell developing an EMF signal indicative of the oxygen content of said gas environment, comprising the steps of, intermittently measuring the EMF signal as an indication of the oxygen content of the gas environment, and, between said intermittent measurements, protecting the sensing electrode by maintaining an oxidizing atmosphere in the gas environment in response to said EMF signal.

* * * * *